United States Patent
Cabot

(10) Patent No.: US 12,426,895 B2
(45) Date of Patent: Sep. 30, 2025

(54) ARRANGEMENT AND METHOD USED IN THE PREPARATION OF BONE SURFACES OF THE KNEE JOINT FOR THE COMPONENTS OF A PROSTHETIC KNEE JOINT

(71) Applicant: Jonathan Peter Cabot, North Adelaide (AU)

(72) Inventor: Jonathan Peter Cabot, North Adelaide (AU)

( * ) Notice: Subject to any disclaimer, the term of this patent is extended or adjusted under 35 U.S.C. 154(b) by 780 days.

(21) Appl. No.: 17/619,435

(22) PCT Filed: Jul. 3, 2020

(86) PCT No.: PCT/AU2020/050702
§ 371 (c)(1),
(2) Date: Dec. 15, 2021

(87) PCT Pub. No.: WO2021/003526
PCT Pub. Date: Jan. 14, 2021

(65) Prior Publication Data
US 2022/0226002 A1 Jul. 21, 2022

(30) Foreign Application Priority Data

Jul. 5, 2019 (AU) .................................. 2019902394
Mar. 31, 2020 (AU) .................................. 2020900986

(51) Int. Cl.
*A61B 17/15* (2006.01)
*A61B 17/02* (2006.01)
(Continued)

(52) U.S. Cl.
CPC .. *A61B 17/157* (2013.01); *A61B 2017/00367* (2013.01); *A61B 2017/00539* (2013.01);
(Continued)

(58) Field of Classification Search
CPC .............. A61B 17/1675; A61B 17/157; A61B 2017/0268; A61F 2002/30556;
(Continued)

(56) References Cited

U.S. PATENT DOCUMENTS 4,211,228 A * 7/1980 Cloutier .................. A61F 2/389
606/88
5,571,194 A * 11/1996 Gabriel ................ A61F 2/3859
623/20.16
(Continued)

FOREIGN PATENT DOCUMENTS

EP 2918235 9/2015
WO 2016065396 5/2016
(Continued)

*Primary Examiner* — David W Bates
(74) *Attorney, Agent, or Firm* — Renner, Kenner, Greive, Bobak, Taylor & Weber

(57) ABSTRACT

An arrangement for minimizing the amount of bone initially required to be resected off surfaces of a knee joint prepared using a plurality of user-operable adjustable extension tabs that define a stability gap derived from gap measurements taken in each of extension, mid-flexion and flexion, wherein the stability gap is commensurate with a reference plane derivable from the arrangement wherein a final bone resection with a corresponding bone surface with said reference plane provides for optimum balanced angular movement between the tibia component and the femoral component of the prosthetic knee joint post-surgery.

19 Claims, 15 Drawing Sheets

(51) Int. Cl.
*A61B 90/00* (2016.01)
*A61F 2/46* (2006.01)
*A61B 17/00* (2006.01)
*A61B 34/00* (2016.01)

(52) U.S. Cl.
CPC ............... *A61B 2017/00544* (2013.01); *A61B 2017/00991* (2013.01); *A61B 2017/0268* (2013.01); *A61B 34/25* (2016.02); *A61B 2090/061* (2016.02); *A61F 2002/4661* (2013.01)

(58) Field of Classification Search
CPC .............. A61F 2/389; A61F 2002/3055; A61F 2002/3863; A61F 2/3859; A61F 2/30734; A61F 2/30736; A61F 2002/4661
See application file for complete search history.

(56) References Cited

U.S. PATENT DOCUMENTS

| | | | | |
|---|---|---|---|---|
| 5,702,460 A * | 12/1997 | Carls | ................. | A61B 17/1764 623/20.14 |
| 6,482,209 B1 * | 11/2002 | Engh | .................... | A61B 17/025 606/88 |
| 10,729,417 B2 * | 8/2020 | Cole | .................... | A61B 5/4528 |
| 11,000,382 B1 * | 5/2021 | Cole | .................... | A61B 5/1121 |
| 11,612,421 B1 * | 3/2023 | Cole | .................... | A61B 17/025 606/105 |
| 11,642,118 B1 * | 5/2023 | Kellar | ...................... | A61F 2/46 606/9 |
| 2004/0249385 A1 * | 12/2004 | Faoro | .................... | A61B 17/157 606/88 |
| 2005/0020941 A1 * | 1/2005 | Tarabichi | ............... | A61B 5/1071 600/587 |
| 2006/0100714 A1 * | 5/2006 | Ensign | .................... | A61F 2/389 623/20.16 |
| 2006/0149277 A1 * | 7/2006 | Cinquin | ............... | A61B 17/025 606/90 |
| 2006/0241569 A1 * | 10/2006 | DiSilvestro | ............. | A61F 2/461 606/1 |
| 2007/0233144 A1 * | 10/2007 | Lavallee | ............. | A61B 17/025 606/90 |
| 2007/0260253 A1 * | 11/2007 | Johnson | ............. | A61B 17/1675 606/79 |
| 2007/0288032 A1 * | 12/2007 | Metzger | ................. | A61F 2/4684 606/99 |
| 2008/0051908 A1 * | 2/2008 | Angibaud | ............... | A61F 2/389 623/20.32 |
| 2013/0138112 A1 * | 5/2013 | Young | .................. | A61B 17/025 606/90 |
| 2013/0267959 A1 * | 10/2013 | Engh | ................ | A61B 17/32002 606/90 |
| 2013/0310838 A1 * | 11/2013 | Kurtz | .................... | A61B 17/157 606/88 |
| 2013/0325136 A1 * | 12/2013 | Thomas | ............. | A61B 17/1735 623/20.32 |
| 2014/0142580 A1 * | 5/2014 | Aram | .................... | A61B 17/157 606/89 |
| 2014/0228853 A1 * | 8/2014 | Rock | .................... | A61B 17/157 606/88 |
| 2014/0296859 A1 * | 10/2014 | Claypool | ............. | A61B 17/157 606/88 |
| 2015/0057756 A1 * | 2/2015 | Lang | ........................ | A61F 2/389 623/18.11 |
| 2015/0105782 A1 * | 4/2015 | D'Lima | ................. | A61F 2/4657 606/90 |
| 2015/0335438 A1 * | 11/2015 | Pierce | ....................... | A61F 2/38 623/20.14 |
| 2016/0106409 A1 * | 4/2016 | Moholkar | ............ | A61B 5/4851 606/90 |
| 2017/0333058 A1 * | 11/2017 | Cabot | ..................... | A61F 2/389 |
| 2018/0177612 A1 * | 6/2018 | Trabish | ................ | A61B 17/025 |
| 2019/0110905 A1 * | 4/2019 | Cabot | .................. | A61B 17/025 |
| 2019/0216608 A1 * | 7/2019 | Cabot | .................. | A61F 2/4657 |
| 2019/0380721 A1 * | 12/2019 | McMinn | ................. | A61F 2/461 |
| 2021/0177439 A1 * | 6/2021 | Culhane | ............... | A61B 17/025 |
| 2021/0212836 A1 * | 7/2021 | Cole | ....................... | G16H 40/67 |
| 2021/0236147 A1 * | 8/2021 | Cabot | .................. | A61F 2/4684 |
| 2022/0175553 A1 * | 6/2022 | Zouaghi | ............... | A61F 2/4684 |
| 2024/0207069 A1 * | 6/2024 | Zouaghi | ............... | A61F 2/3868 |
| 2024/0238102 A1 * | 7/2024 | Nonnenmann | ......... | A61F 2/389 |

FOREIGN PATENT DOCUMENTS

| | | |
|---|---|---|
| WO | 2019115744 | 6/2016 |
| WO | 2017181216 | 10/2017 |
| WO | 2017197462 | 11/2017 |

* cited by examiner

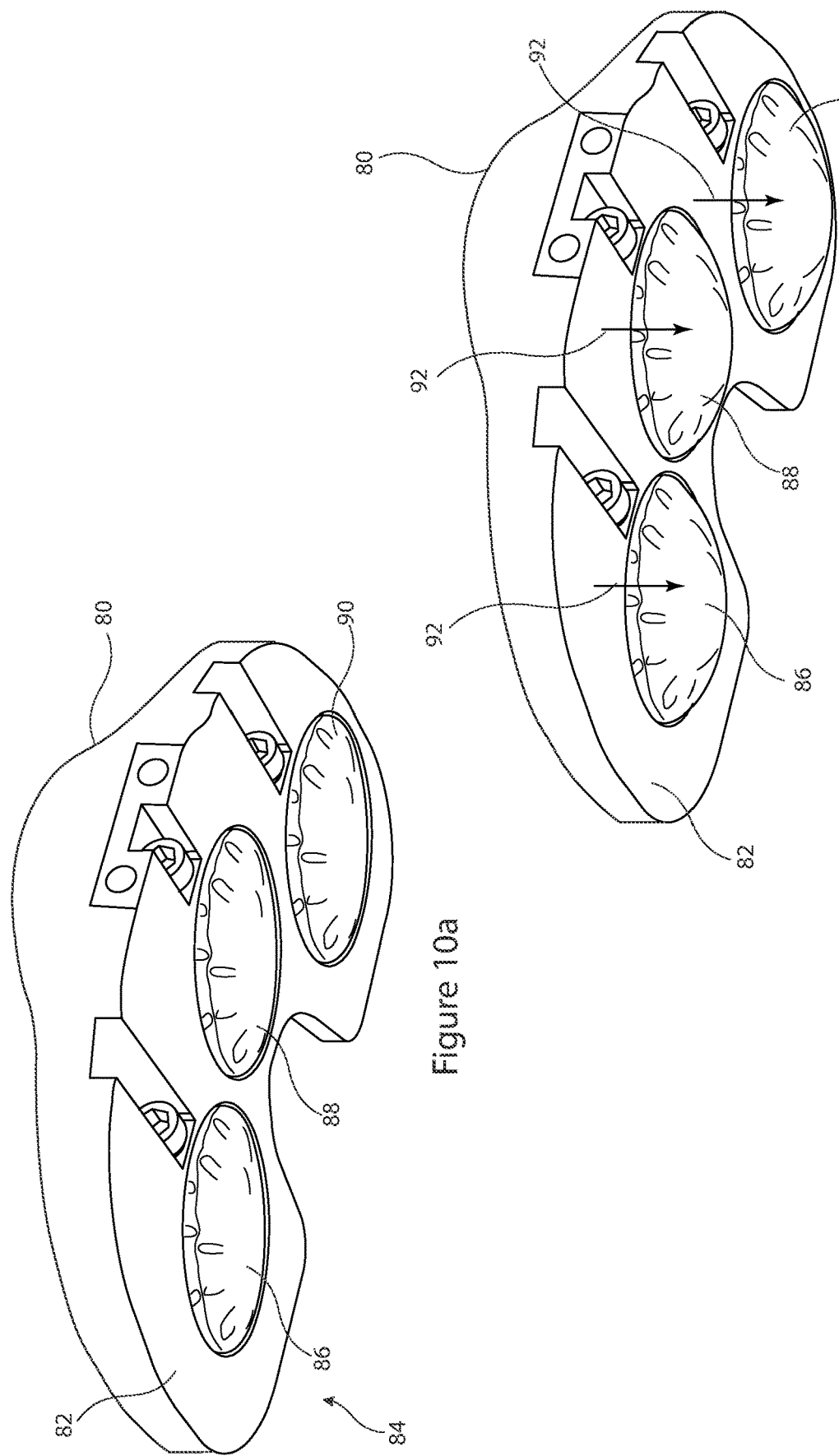

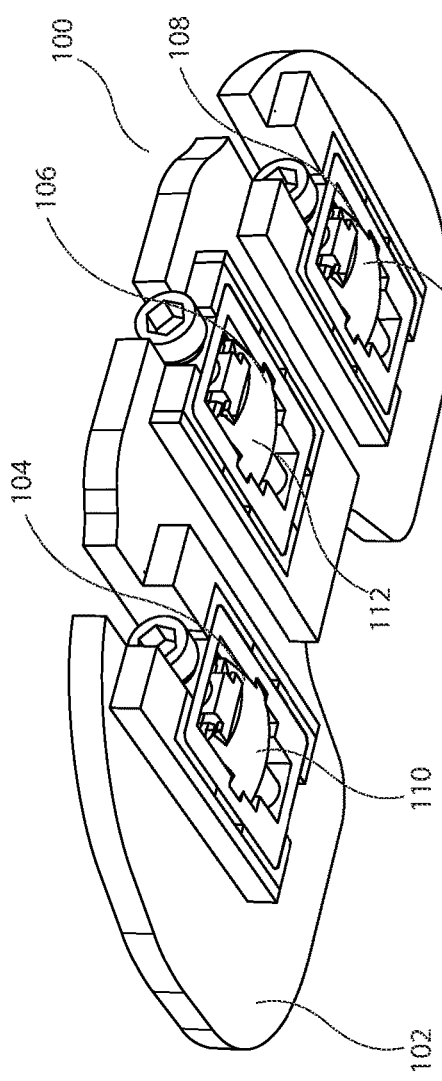
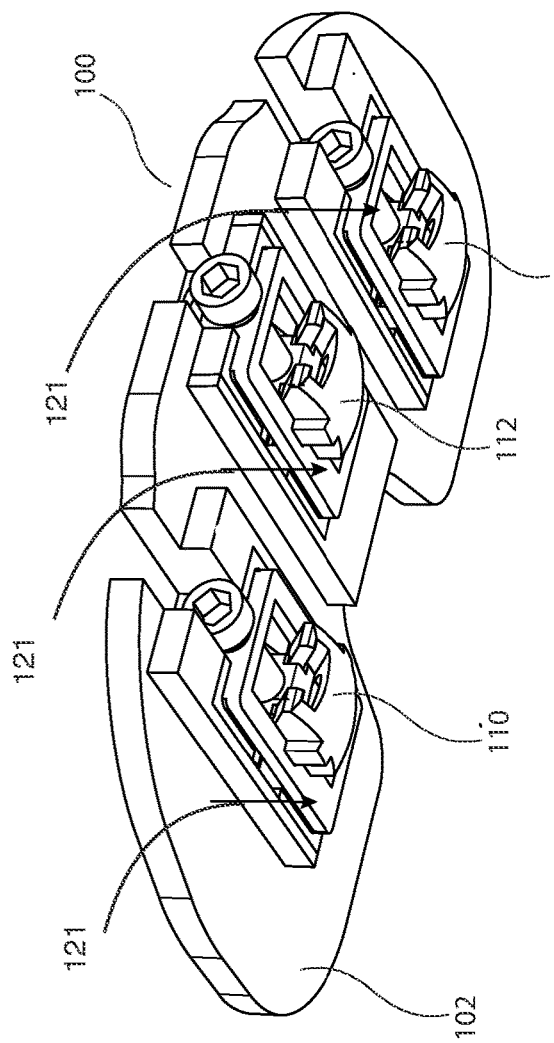

ARRANGEMENT AND METHOD USED IN THE PREPARATION OF BONE SURFACES OF THE KNEE JOINT FOR THE COMPONENTS OF A PROSTHETIC KNEE JOINT

TECHNOLOGICAL FIELD

This invention relates to improved arrangements and methods in the preparation of the proximal surface of the tibia and/or the distal femur and the posterior femoral condyle proximal surfaces for the components of a prosthetic knee joint. More particularly this invention relates to minimizing the amount of bone initially required to be resected off these surfaces in preparations for the components of the prosthetic knee joint.

BACKGROUND ART DISCUSSION

The applicant as disclosed in WO2016/065396 and WO2017/181216 recognized the significance of establishing a 'tibia reference plane' that was defined by the orientation of the underside of a joint liner, wherein this tibia referenced plane when replicated as a final bone resection cut of the proximal surface of the tibia provided the necessary surface profile that optimized the required balance and stability between the tibia and femoral components of the prosthetic knee joint.

The ability to achieve this favourable profiling of the top surface of the tibia through the use of the 'tibia reference plane' relied upon an arrangement that utilised an adjustable tibia preparation plate. This adjustable tibia preparation plate included operable height adjustable extension tabs that assisted in establishing the tibia reference plane by engagement of these user-operable height adjustable extension tabs with the underside of the joint liner.

While the applicant's previous inventions through the use of the tibia preparation plate and notably the defining of the 'tibia reference plane' by the operable height adjustable extension tabs was advantageous, problems arise because in order to accommodate both the joint liner and the tibia preparation plate this meant that extra spacing was required between the ends of the tibia and the femur so that these components could be inserted therein.

Preference to a surgeon would be to minimize the amount of bone that is required to be initially cut off the end of the tibia so there remains a need to utilise the benefits of establishing 'the tibia reference plane' that was achievable through the use of the operable height adjustable extension tabs that were enclosed in the tibia preparation plate of the applicant's earlier inventions, but to achieve this outcome without the need of unnecessarily initially cutting off too much of the surface of the tibia than would generally otherwise be required.

Further the applicant, by way of WO2017197462, was also able to previously provide methods and arrangements for the balancing of the femoral side of the prosthetic knee joint for optimum final bone resection of the distal end of the femur and also the posterior femoral condyle, and other femoral cuts to accommodate the femoral component.

As discussed in WO2017197462 the unique use of the generally L shaped femoral tibia stability gap alignment clamp provided a vertical arm with associated lateral extension tabs which were responsible for providing the requisite distal end of the femur reference plane through the engagement with the front plate, and the horizontal arm with the associated height extension tabs makes the necessary adjustments to the base plate (and/or separate sections of the base plate) to establish the requisite posterior condylar reference plane so that if the final resection of each of the distal end of the femur and the posterior femoral condyle where cut to expose surfaces with the same profile of these reference planes, this then allows the femoral component of the prosthetic knee joint to operate optimally.

While the applicant's previous invention, through the use of the generally L shaped femoral tibia stability gap alignment clamp define the required reference planes by the operable height extension tabs on the horizontal arm and the lateral extension tabs on the vertical arm, problems arise because in order to accommodate both the conventional front plate or standard femoral component and the generally L shaped femoral tibia stability gap alignment clamp this meant that extra spacing was required between the ends of the tibia and the femur so that both these components could be inserted therein.

Once again preference to a surgeon is to minimise the amount of bone that is required to be initially cut off the ends of the surface of the femur so there remains a need to utilise the benefits of establishing 'the femur reference planes' that was achievable through the use of the operable height adjustable extension tabs and lateral extension tabs that were part of the generally L shaped femoral tibia stability gap alignment clamp of the applicant's earlier invention, but to achieve this outcome without the need of unnecessarily initially cutting off too much of the surface of the end of the femur surfaces than would generally otherwise be required.

Accordingly it is an object of this invention to still provide an arrangement and method of establishing a tibia reference plane utilizing operable height adjustable extension tabs but to do so by minimizing the spacing required between the ends of the tibia and the femur to accommodate the necessary componentry to establish the tibia reference plane thereby resulting in minimizing the depth that is required to be cut off the proximal surface of the tibia during the initial resection as part of the surgery.

Accordingly it is a further object of this invention to still provide an arrangement and method of establishing the femur reference planes utilizing operable height and lateral adjustable extension tabs but to do so by minimizing the spacing required between the ends of the tibia and the femur to accommodate the necessary components to establish the femur reference planes thereby resulting in minimizing the depth that is required to be cut off the end of the femur surfaces during the initial resection as part of the surgery.

Further objects and advantages of the invention will become apparent from a complete reading of the following specification.

SUMMARY OF THE INVENTION

In one form of the invention there is provided an arrangement for the preparation of the proximal surface of the tibia for a tibia component of a prosthetic knee joint, said arrangement including:

a joint liner, said joint liner including an upper articulated surface to engage a femoral component of a knee joint, said joint liner further including a plurality of user-operable height adjustable extension tabs, wherein the plurality of user-operable height adjustable extension tabs are height adjustable from an underside of said joint liner, such that a height adjustment of said plurality of user-operable height adjustable extension tabs defines a stability gap derived from gap measurements taken in each of extension, mid-flexion and flexion, wherein the stability gap is commensurate with a tibia reference plane defined on an underside surface of the joint liner, wherein a final bone resection of the proximal surface of the tibia consistent with said tbia reference plane provides for balanced angular movement between the tibia component and the femoral component of the prosthetic knee joint throughout an arc motion from extension, mid-flexion and flexion.

An advantage of such an arrangement is that as the user-operable height adjustable extension tabs are positioned on the underside of the joint liner there is no need for the separate requirement of an additional preparation plate that previously would have included the height adjustable extension tabs.

With the elimination of the separate preparation plate that includes the height adjustable extension tabs means that the spacing required for the componentry to prepare the appropriate preparation of the proximal surface of the tibia through establishing the 'tibia reference plane' can be reduced thereby minimizing the depth or amount of bone that needs to be initially cut off the end of tibia by the surgeon.

Previously as disclosed in patents WO2016/065396 and WO2017/181216, the tibia and femoral stability gap preparation plate that included the user-operable height adjustable extension tabs was adapted to rest upon that initially resected proximal surface of the tibia but advantageously for this invention the preparation plate is eliminated but the required definable reference plane is still made possible because uniquely the user-operable height adjustable extension tabs, when height is adjusted to create the reference plane, extend directly out from the underside of the joint liner to engage with the surface of the initially resected tibia, or alternatively in other embodiments if necessary a very fine plate, film or the like, restable on the initially resected proximal surface of the tibia, which can prevent compression bores caused by the height adjustable extension tabs pushing down upon the surface of the initially resected tibia during adjustment.

In the event the surgeon cuts of too much tibia bone for the initial resection of the surface of the tibia, then a spacer or the like can be placed on the surface of the initially cut surface of the tibia. If need be the height of the spacer can also be adjustable.

In preference the joint liner includes a pressure sensor arrangement. Preferably the pressure sensor arrangement is included into the main body of the joint liner or a series of sensors are included in the user-operable height adjustable extension tabs.

In preference the arrangement is in communication with a controller to record, calculate and/or display pressure measurement derived from the pressure sensor arrangement.

In preference the arrangement includes a display unit to visually display thereupon the knee joint and associated tibia and femur.

In preference the display unit includes functionality for 3D modelling of the knee joint, femur and tibia upon a visual display unit In preference the joint liner includes a plurality of slots on the underside of the joint liner in which corresponding user-operable height adjustable extension tabs can be enclosed or at least substantially enclosed therein.

Advantageously, in this preferred embodiment further space savings and thereby further minimization of initial tibia bone resection is achievable, in that as the starting point of height adjustability has the underside bottom surface of the joint liner simply resting upon that initial resected tibia bone top surface means that as the plurality of user-operable height adjustable extension tabs are extended out from the underside of the joint liner, this extension of the tabs comes from a flushed starting point emanating from the bottom surface of the underside of the joint liner.

In preference the plurality of user-operable height adjustable extension tabs includes three operable height adjustable extension tabs and wherein the joint liner includes three corresponding slots wherein each respective slot of the joint liner encloses a corresponding user-operable height adjustable extension tab.

In preference each user-operable height adjustable extension tab is drivable to an extended/retracted position utilising mechanical, hydraulic, electrical, electronic and/or a pneumatic drive action.

In preference each user-operable height adjustable extension tab is in communication with a corresponding user-engageable knob, wherein adjustability of the user-engageable knob by way of rotational and/or vertical movement provides for an extension/retraction of the corresponding user-operable height adjustable extension tab.

In an alternative embodiment, each operable height adjustable extension tab is remotely operable by way of electromagnetic radiation signals to remotely control the extension and retraction of the user-operable height adjustable extension tabs to and from the underside and/or enclosed slot on the underside of the joint liner.

In preference each user-operable height adjustable extension tab includes a bladder wherein the bladder provides for the extension of the user-operable height adjustable extension tab from the underside of the joint liner and deflation of the bladder arrangement retracts the user-operable height adjustable extension tab back towards and/or within the underside of the joint liner.

In preference to the bladder is aerated or fluid controlled, including hydraulics.

In preference the expansion and deflation of the bladder through aeration is provided by pneumatics.

In an alternative embodiment, preferably each user-operable height adjustable extension tab is telescopically extendable and retractable to and from the underside of the joint liner or from within corresponding slots located on the bottom side of the underside of the joint liner.

In an alternative embodiment of the invention the arrangement, rather than including the plurality of the user-operable height adjustable extension tabs extendable out from the underside of the joint liner, would include a separate plate adapted to engage with the underside of a joint liner and wherein this separate plate would include slots there within which would house corresponding user-operable height adjustable extension tabs.

In this alternative form of the invention, although the arrangement further includes a separate plate to the joint liner, space savings still become achievable in that the user-operable height adjustable extension tabs within their retracted position remain completely enclosed within the slots on the underside of the preparation plate.

Therefore the preparation plate is able initially to remain flush with the surface of the initially resected proximal surface of the tibia with height adjustment achieved by user engagement with the user-operable height adjustable extension tabs to extend thereout from the underside of the separate preparation plate to engage with the surface of the initially resected tibia but nonetheless height adjustment of the respective operable height adjustable extension tabs extending out from the preparation plate still will then orientate the underside of the joint liner so as to establish that required definable reference plane which then would be replicated as the final cut profile to the proximal surface of the tibia.

The main focus of this invention, as introduced above, is the ability to minimize the required spacing to accommodate those components which assist in establishing the defined reference plane which will ultimately then be resected as the final cut on the proximal surface of the tibia.

The actual arrangements and methods in translating that established reference plane are not essential to the main technical concept of this invention but can include the following preferred methods.

In a preference the final bone resection of the proximal surface of the tibia includes an electronic system arrangement including an input signal, wherein the input signal into the electronic system arrangement provides a tibia reference plane measured data information, wherein the tibia reference plane measured data information includes the orientation in space, angle and/or positioning of the tibia reference plane defined by the underside of the joint liner;

said electronic system arrangement configured to respond to the inputted signal of the tibia reference plane measured data information to communicate electrical energy in the form of an output action to align a blade and/or cutting implement at an angle such that resecting of the bone across at or below the proximal surface of the tibia at the alignment of the blade and/or cutting implement provided by the tibia reference plane measured data information replicates the tibia reference plane on the proximal surface of the final resected tibia.

In an alternative embodiment the final bone resection of the proximal surface of the tibia includes a tibia cutting guide arrangement, said final bone resection of the proximal surface of the tibia cutting guide arrangement including a cutting guide having an indicator, wherein the indicator provides a reference guide for a cutting blade or saw to cut the final bone resection of the proximal surface of the tibia and wherein said joint liner and said final bone resection of the proximal surface of tibia cutting guide arrangement including a mounting arrangement, wherein the mounting arrangement is configured to provide a first mounted position between said joint liner and said final bone resection of the proximal surface of tibia cutting guide arrangement, wherein the indicator of the cutting guide is aligned with the same referenced plane as the referenced plane defined by the underside of the joint liner and wherein said mounting arrangement further configured to provide a second mounted position wherein the indicator of the cutting guide aligned with the same referenced plane of the underside of the joint liner is adjustable below the initial resected proximal surface of the tibia.

In preference the mounting arrangement is configured to provide the first mounted position between the tibia and femoral stability gap preparation plate by at least one slot and at least a corresponding lug.

In preference the joint liner includes at least one slot and the final bone resection of the proximal surface of the tibia cutting guide arrangement includes a or corresponding lug for the or each slot or wherein the joint liner includes at least one lug and the final bone resection of the proximal surface of the tibia cutting guide arrangement includes a or corresponding slot for the or each lug.

In preference there are at least a pair of slots on the front side of the joint liner and a pair of corresponding lugs protruding out from the front of the final bone resection of the proximal surface of the tibia cutting guide arrangement or wherein there are at least a pair of lugs protruding out a front side of the joint liner and a pair of corresponding slots in the final bone resection of the proximal surface of the tibia cutting guide arrangement.

In preference the mounting provides the second mounted position by including a vertical support, wherein the vertical support allows the cutting guide to be vertically adjustable there along said vertical support.

In preference the vertical support is adapted to incrementally adjust and position the cutting guide vertically there along said vertical support.

In preference the vertical incremental adjustment of the cutting guide along the vertical support includes a ratchet arrangement.

In further embodiments of the invention the vertical incremental adjustability of the cutting guide along the vertical support can include a clutch, intermediate gearing and cams.

In preference the indicator of the cutting guide includes a slot where in a saw or blade to complete the final bone resection of the proximal surface of the tibia is guidable into said slot of the indicator of the cutting guide so as to orientate the saw or blade to cut the proximal surface of the tibia with a commensurate profile to the established reference plane on the underside of the joint liner.

In a further form of the invention there is provided an arrangement for providing the proximal surface of the distal end of the femur and the posterior femoral condyle of the femur for a femoral component of a prosthetic knee joint, said arrangement including:

a femoral component mountable to the femur such that a vertical section of the femoral component is adapted to be aligned with the distal end of the femur and a horizontal section of the femoral component is adapted to be aligned with a posterior femoral condyle of the femur;

said vertical section of the femoral component including user-operable lateral adjustable extension tabs, wherein each user-operable lateral adjustable extension tab is adapted to engage an initially resected distal end of the femur, such that lateral adjustment of the femoral component by said plurality of user-operable lateral adjustable extension tabs defines a stability gap derived from gap measurements taken in each of extension, mid-flexion and flexion, wherein the stability gap is commensurate with a femur reference plane defined by the vertical section of femoral component, wherein a final bone resection of the distal end of the femur with a profile of the distal end of the femur reference plane provides balanced angular movement between the tibia component and the femoral component of the prosthetic knee joint throughout an arc of motion from extension, mid-flexion and flexion post surgery;

said horizontal section of the femoral component including user-operable height adjustable extension tabs, wherein the user-operable height adjustable extension tabs of the femoral component are adapted to engage an initially resected surface of the posterior femoral condyle of the femur, such that adjusting the vertical height of the horizontal section of the femoral component by said plurality of user-operable height adjustable extension tabs upon the initially resected surface of the posterior femoral condyle of the femur defines a stability gap derived from gap measurements taken in each of extension, mid-flexion and flexion, wherein the stability gap is commensurate with a posterior femoral condyle reference plane upon the horizontal section of the femoral component, wherein final bone resection with the posterior femoral condyle referenced plane to the posterior femoral condyle of the femur provides for balanced angular movement between the femoral component and the tibia component of the prosthetic knee joint throughout an arc of motion from extension, mid-flexion and flexion.

In preference the femoral component has a C shape.

In preference the C shape includes the vertical section in between the horizontal section at the base of the C shape and a corresponding top section at a top of the C shape.

In an alternative embodiment of the invention the femoral component is an L shape.

In preference a vertical arm of the L shape provides for the vertical section and a horizontal arm of the L shape provides for the horizontal section.

In still a further form of the invention there is provided an arrangement for providing the proximal surface of the distal end of the femur and the posterior femoral condyle of the femur for a femoral component of a prosthetic knee joint, said arrangement including:

a generally L shaped femoral clamp including a rear side mountable to the femur and a front side engageable with a femoral component, a vertical arm of the generally L shaped femoral clamp including user-operable lateral adjustable extension tabs at least partially contained within the rear side of the vertical arm in a retracted position, wherein lateral adjustment by said plurality of user-operable lateral adjustable extension tabs at measurements taken at extension, mid-flexion and flexion provides a distal end of the femur reference plane defined by the vertical arm of the generally L shaped femoral clamp, wherein a final bone resection of the distal end of the femur with a profile of the distal end of the femur reference plane provides balanced angular movement between the tibia component and the femoral component of the prosthetic knee joint throughout an arc of motion from extension, mid-flexion and flexion post surgery; and a horizontal arm of the L shaped femoral clamp including user-operable height adjustable extension tabs at least partially contained within a top surface of the horizontal arm, wherein the user-operable height adjustable extension tabs are adapted to engage an initially resected surface of the posterior femoral condyle of the femur, such that adjusting the vertical height of the horizontal section of the L shaped femoral clamp by said plurality of user-operable height adjustable extension tabs upon the initially resected surface of the posterior femoral condyle of the femur at measurements taken at extension, mid-flexion and flexion defines a posterior femoral condyle reference plane upon the horizontal arm of the L shaped femoral clamp, wherein final bone resection with the posterior femoral condyle referenced plane to the posterior femoral condyle of the femur provides for balanced angular movement between the femoral component and the tibia component of the prosthetic knee joint throughout an arc of motion from extension, mid-flexion and flexion.

In preference each user-operable height adjustable extension tab and each user-operable lateral adjustable extension tab is drivable to an extended/retracted position utilising mechanical, hydraulic, electrical, electronic and/or a pneumatic drive action.

In preference each user-operable height adjustable extension tab and each user-operable lateral adjustable extension tab is in communication with a corresponding user-engageable knob, wherein adjustability of the user-engageable knob by way of rotational and/or vertical movement provides for an extension/retraction of the corresponding user-operable height adjustable extension tab.

In preference each operable height adjustable extension tab and each user-operable lateral adjustable extension tab is remotely operable by way of radio signals to remotely control the extension and retraction of the user-operable height adjustable extension tabs to and from the underside and/or enclosed slot on the underside of the joint liner.

In preference each user-operable height adjustable extension tab and each user-operable lateral adjustable extension tab includes a bladder wherein expanding the bladder provides for the extension of the user-operable height adjustable extension tab and each user-operable lateral adjustable extension tab.

In preference the expanding and deflation of the bladder is by aeration and/or fluid control, and wherein aeration is provided by pneumatics.

In preference each user-operable height adjustable extension tab and each user-operable lateral adjustable extension tab is telescopically extendable and retractable.

In preference the final bone resection includes a robotic cutter.

In preference further including a pressure sensor arrangement.

In order now to describe the invention in greater detail a series of preferred embodiments of the invention will be shown with the assistance of the following illustrations and accompany text.

BRIEF DESCRIPTION OF THE DRAWINGS

FIGS. 1a and 1b show front underside perspective views of the joint liner in a preferred embodiment of the invention wherein FIG. 1a shows the user-operable height adjustable extension tabs in a retracted position within the underside of the joint liner and wherein FIG. 1b shows the user-operable height adjustable extension tabs in a user adjusted extended position from the underside of the joint liner.

FIGS. 10a and 10b show an alternative preferred embodiment of the user-operable height adjustable extension tabs of this invention wherein FIG. 10a shows the user-operable height adjustable extension tabs in a retracted position and wherein FIG. 10b shows the user-operable height adjustable extension tabs in an extended position out from the underside of the joint liner.

FIGS. 11a and 11b show a further preferred embodiment of the user-operable height adjustable extension tabs wherein FIG. 11a shows the user-operable height adjustable extension tabs in the retracted position and FIG. 11b showing the user-operable height adjustable extension tabs in the extended position.

FIGS. 12a and 12b show an alternative embodiment of the invention wherein the user-operable height adjustable extension tabs are incorporated into a separate preparation plate to extend out therefrom the underside of the preparation plate wherein FIG. 12a shows the user-operable height adjustable extension tabs in the retracted position and in the extended position in FIG. 12b.

FIG. 13b is a front perspective view of FIG. 13a.

FIG. 14b is a front perspective view of the rear perspective view shown in FIG. 14a.

DETAILED DESCRIPTION OF THE DRAWINGS

Figure 1:
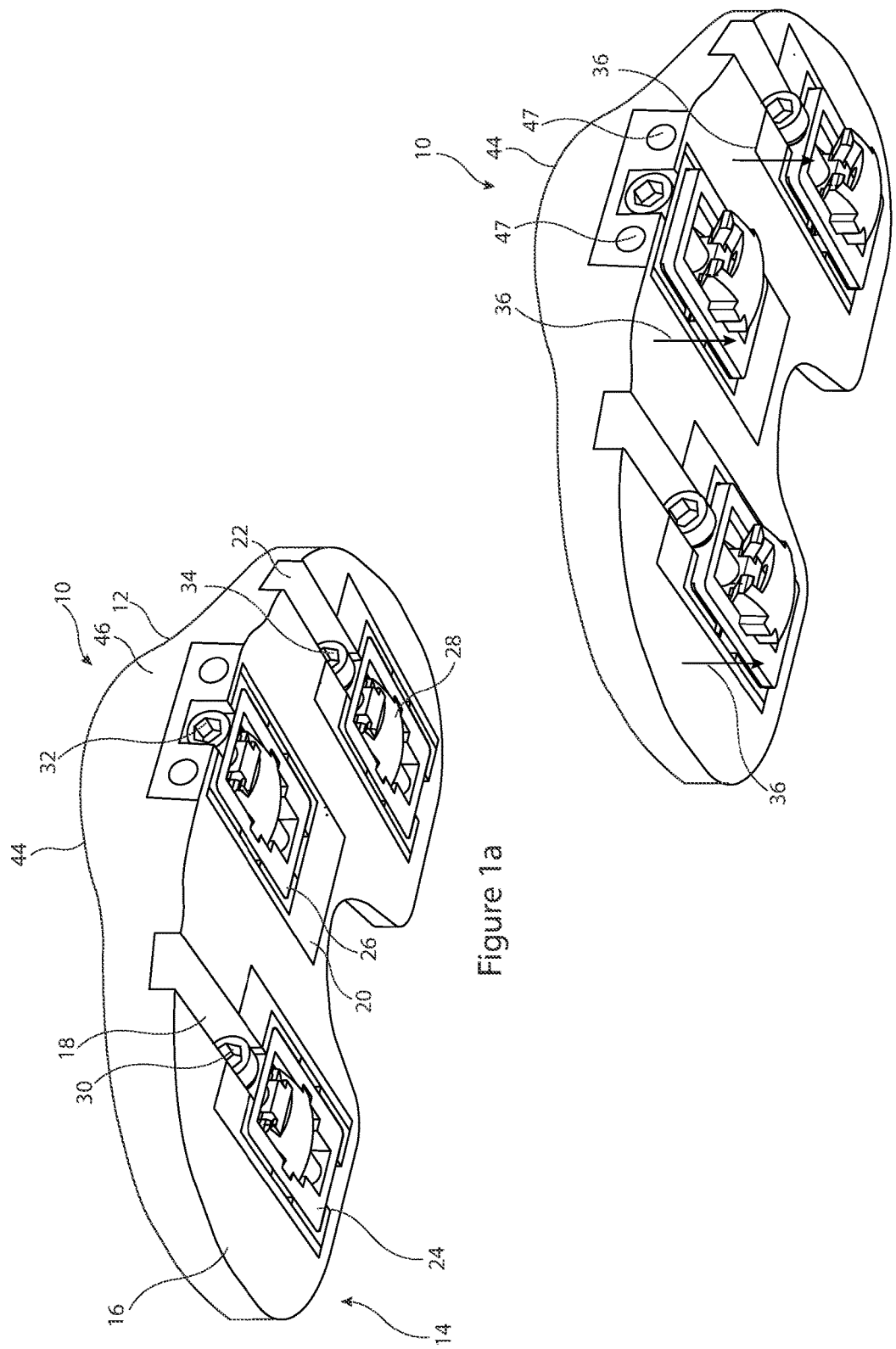
Figure 2:
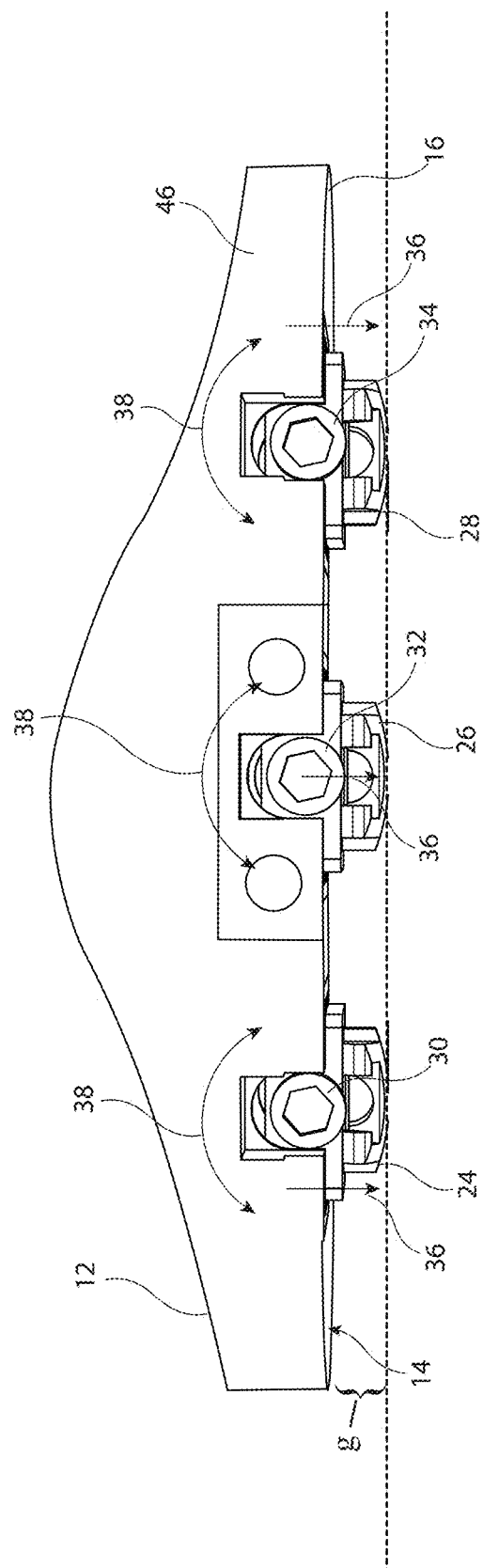
FIG. 2 is a front view of the joint liner with the user-operable height adjustable extension tabs in an extended position out from the bottom surface of the underside of the joint liner.

Referring to the drawings now in greater detail and notably at first instance to FIGS. 1a, 1b and FIG. 2.

The arrangement for the preparation of the proximal surface of the tibia for the tibia component of the prosthetic knee joint in the preferred embodiment is shown generally as (10).

The arrangement includes a joint liner (12) wherein the joint liner (12) has an underside shown generally as (14) and a bottom surface (16) on the underside (14) of the joint liner (12).

The underside (14) of the joint liner (12) includes a series of slots (18, 20 and 22) which enclose corresponding user-operable height adjustable extension tabs (24, 26 and 28).

Figure 3:
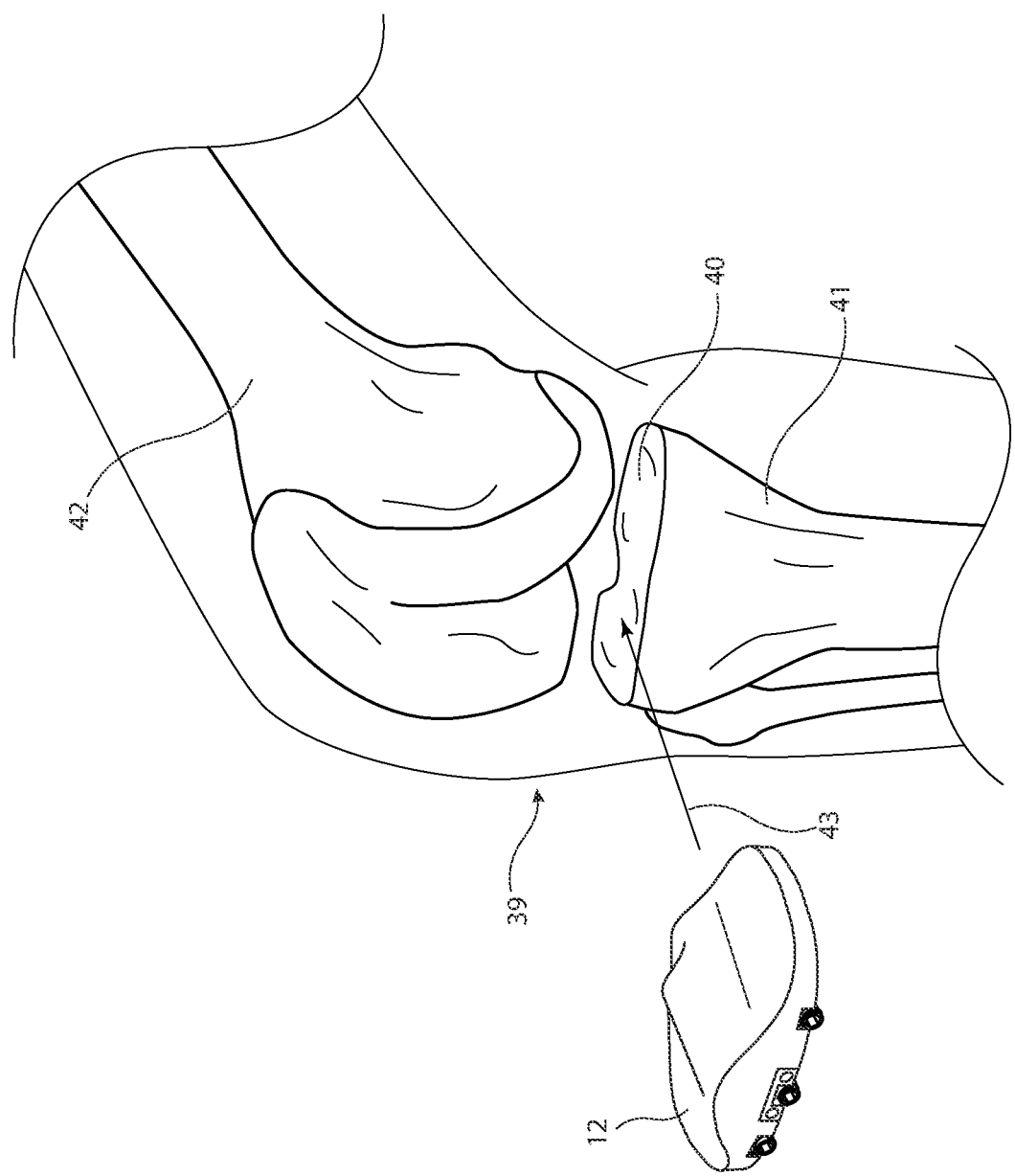
FIGS. 3 to 9 are schematic representations showing the use of the arrangement for the preparation of the proximal surface of the tibia in a preferred embodiment of the invention.
Figure 9:
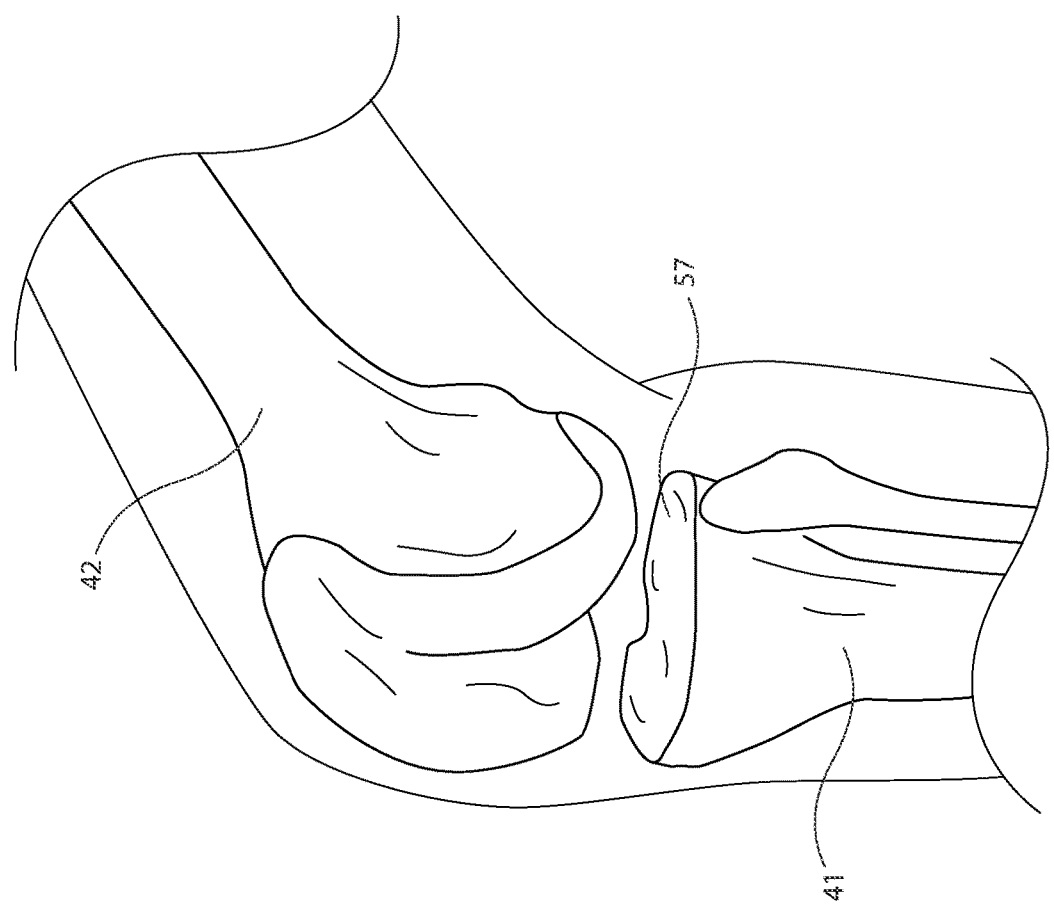

These user-operable height adjustable extension tabs (24, 26 and 28) are in a retracted enclosed position as shown in FIG. 1a but can be extended thereout as shown in FIG. 1b and FIG. 2 so as to be height adjusted to create that requisite stability gap as a measurement taken in each of extension, mid-flexion and flexion, wherein the stability gap is commensurate with the reference plane which will become definable as to the orientation on the underside of the joint liner which will be discussed in greater detail when referencing FIG. 3 through to FIG. 9 shortly hereafter.

In the preferred embodiment shown in FIGS. 1a, 1b and 2 the user-operable height adjustable extension tabs (24, 26 and 28) are extendable and retractable by a user engaging with the knobs (30, 32 and 34).

As shown by way of arrows (36 and 38) in FIGS. 1b and 2, by rotating the knobs (30, 32 and 34) this can extend the corresponding user-operable height adjustable extension tabs (24, 26 and 28) from the bottom side (16) located on the underside (14) of the joint liner (12).

Nonetheless the significance of this preferred embodiment of the invention lies in the introduction of having the user-operable height adjustable extension tabs (24, 26 and 28) enclosed within the joint liner (12) as opposed to being part of any separate plate arrangement.

Advantageously, not only are the user-operable height adjustable extension tabs (24, 26 and 28) located on the underside (14) of the joint liner (12) as opposed to a separate preparation plate, they are also contained and enclosed within slots (18, 20 and 22) defined into the bottom surface (16) of the underside (14) of the joint liner (12).

Incorporating the user-operable height adjustable extension tabs (24, 26 and 28) to the joint liner (12) and also enclosing them further into the slots (18, 20 and 22) means that it is now possible to minimize the spacing required to handle the componentry to appropriately prepare the proximal surface of the tibia so that the final resected surface of the tibia will provide for the optimum balance and stability for the tibia component and/or the femoral component of the prosthetic knee joint to permit stable and balance movement of the knee joint through the entire angular movement from extension, mid-flexion and through to flexion and then back again.

In relation to FIGS. 3-9 the illustrations need to be placed in the context of the intended outcome achieved through the use of arrangement and methods provided for in this invention Orthopaedic surgeons during surgery aim to provide balance, unobstructed movement of the knee components for the complete arc of motion from extension, mid-flexion and flexion and then back again.

Accordingly, the final bone resection of the proximal surface of the tibia is required to be cut correctly in order to present the appropriate profile to the tibia component positioning in the knee arthroplasty whether that be a total knee or uni-compartmental knee operation.

FIG. 3 shows a knee joint generally as 39.

A cutter (not shown), has prepared the initial resection of the proximal surface 40 of the tibia 41. The general distal end of the femur 42 is also shown. In FIG. 3 the joint liner 12 shown by way of arrow 43 is being inserted onto the initially resected proximal surface 40 of the tibia 41.

From FIG. 3 it can be realised that the general shape and dimensions of the bottom surface 16 of the joint liner 12 is of a comparative dimension of the proximal surface 40 of the tibia 41.

Figure 4:
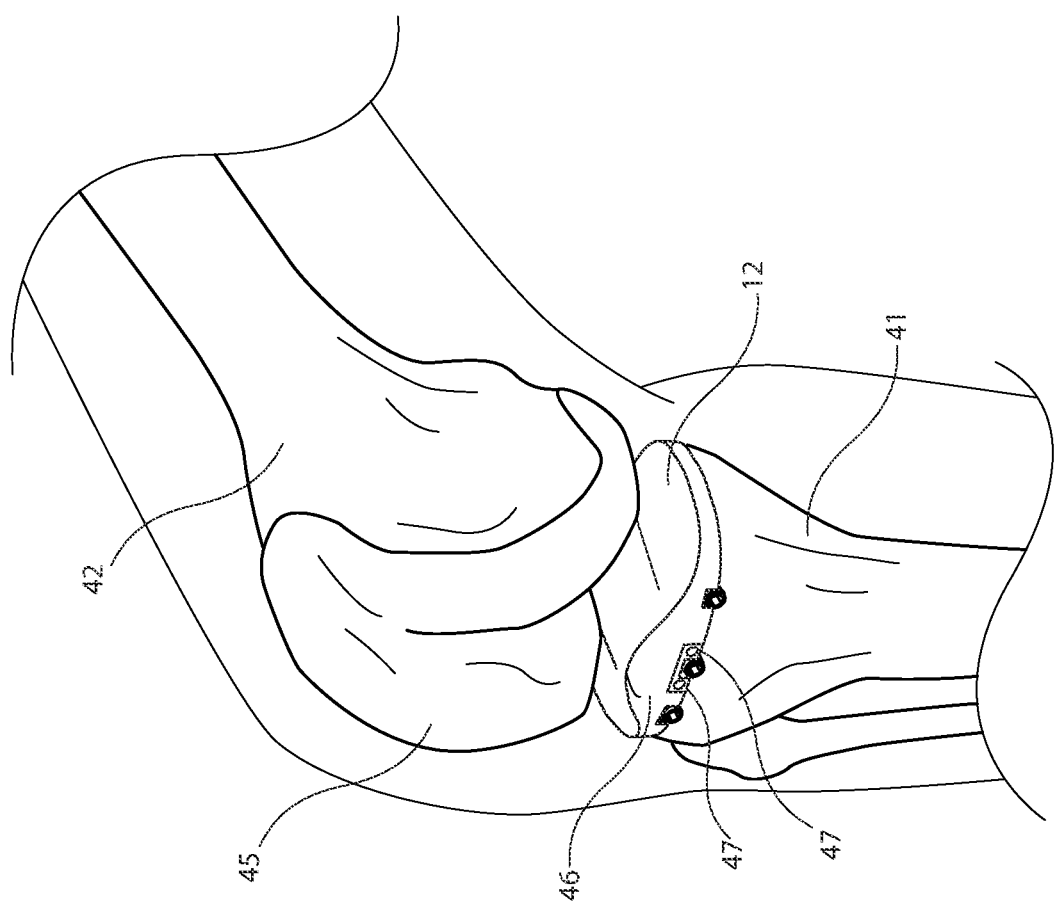

FIG. 4 shows the actual positioning of the joint liner 12 on the proximal surface 40 of the tibia 41 sandwiched therein between the femoral component 42 and the tibia 41.

The joint liner 12 has an articulated upper surface 44 to engage the femoral component 45 of the femur 42.

Importantly, the joint liner 12 on the front side 46 includes a pair of slots 47 of which will be discussed in greater detail when referencing the mounting arrangement between the joint liner 12 and the final bone resection proximal surface of the tibia cutting guide arrangement 48 which is introduced in FIG. 6.

Figure 5:
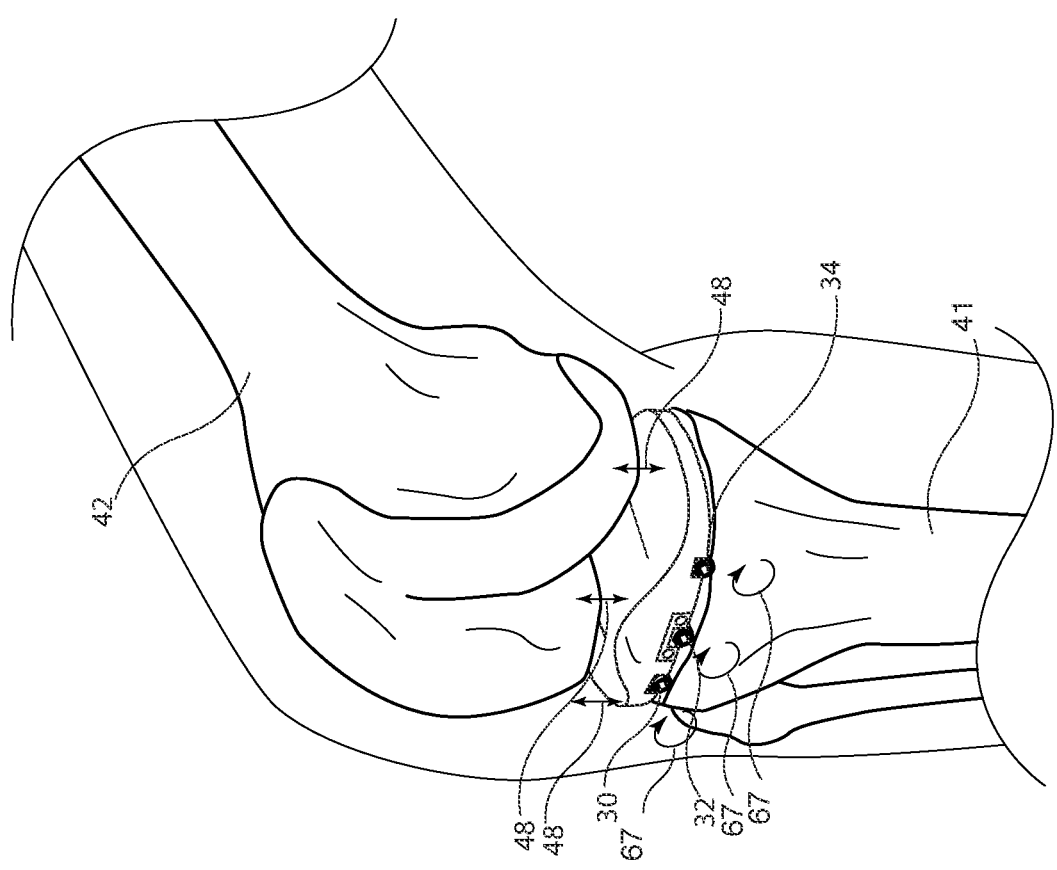

FIG. 5 shows the knee joint at mid-flexion. Operable knobs 30, 32 and 34 when rotated by way of arrows 67, 67 and 67 adjust the height of the corresponding user-operable height adjustable extension tabs (24, 26 and 28) that extend out (not shown in FIG. 5) from the underside of the joint liner (12) which then also adjusts the orientation, the reference plane, of the bottom surface 16 of the underside 14 of the joint liner 12. The arrows 48 in FIG. 5 represent the upward movement of the joint liner 12 and the orientation of the bottom surface 16 of the underside 14 of the joint liner 12.

This height adjustability although not shown in the illustrations would also have been completed at extension, mid flexion and then ultimately at flexion or 90 degrees.

Accordingly, the user operable height adjustable extension tabs 24, 26 and 28 create a triangular support of the top surface 40 of the tibia 41, which then aligns and/or orientates the bottom surface 16 on the underside 14 of the joint liner 12 accordingly. The stability gap that has been established is commensurate with the references plane that has now been established on the bottom surface 16 on the underside 14 of the joint liner 12 through the height adjustability of the height adjustable extension tabs 24, 26 and 28 from extension, mid-flexion and flexion.

Hence albeit measurements of the height adjustability of the height adjustable extension tabs 24, 26 and 28 from extension, mid-flexion and flexion provides for a stability gap, this stability gap is then represented by the referenced plane now provided for on the bottom surface 16 on the underside 14 of the joint liner 12.

With the referenced plane now established on bottom surface 16 on the underside 14 of the joint liner 12, the aim is then to translate that reference plane as the final bone resection of the proximal surface of the tibia, which is achieved by using a cutting guide arrangement 48 which is then mountable to the joint liner 12.

Figure 6:
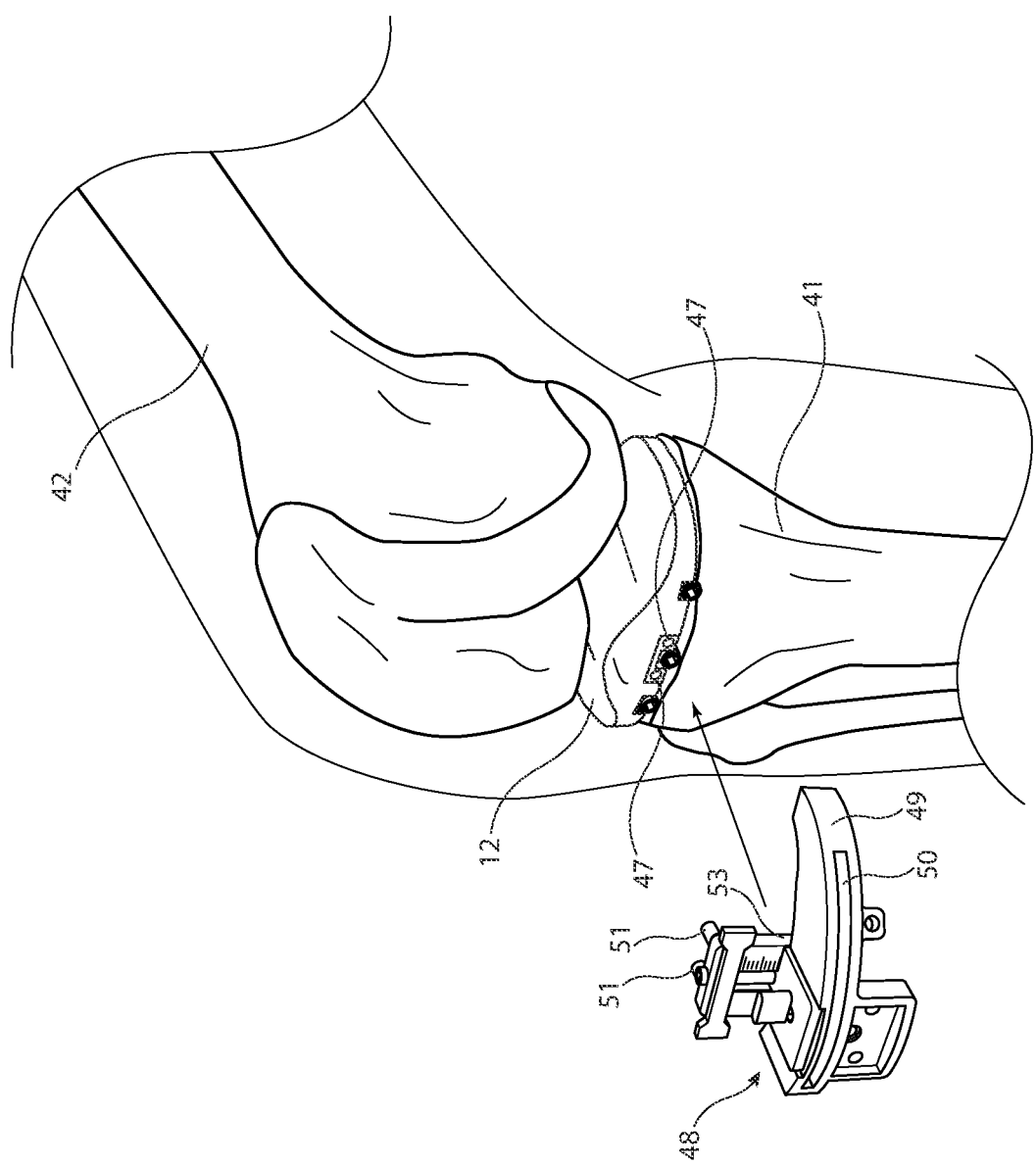

The final bone resection of the proximal surface of the tibia cutting guide arrangement 48, as best seen in FIG. 6, includes a cutting guide 49, wherein the cutting guide 49 includes an indicator in the form of a slot 50.

The purpose of the slot 50 is that it will allow the blade or a saw to be guided to make a final resection cut of the proximal surface of the tibia in the orientation as to the alignment of the slot 50.

It is therefore a requirement that the indicator, which in this preferred embodiment is a slot 50 included as part of the cutting guide 49 is aligned the same as the bottom surface 16 on the underside 14 of the joint liner 12.

The final bone resection of the proximal surface of the tibia cutting guide arrangement 48 as part of the mounting arrangement between the final bone resection of the proximal surface of the tibia cutting guide arrangement 42 and the joint liner 12 includes a pair of lug extensions or protrusions 51, which are adapted to be slotted to the corresponding pair of slots 47 on the front side 46 of the joint liner 12.

Figure 7:
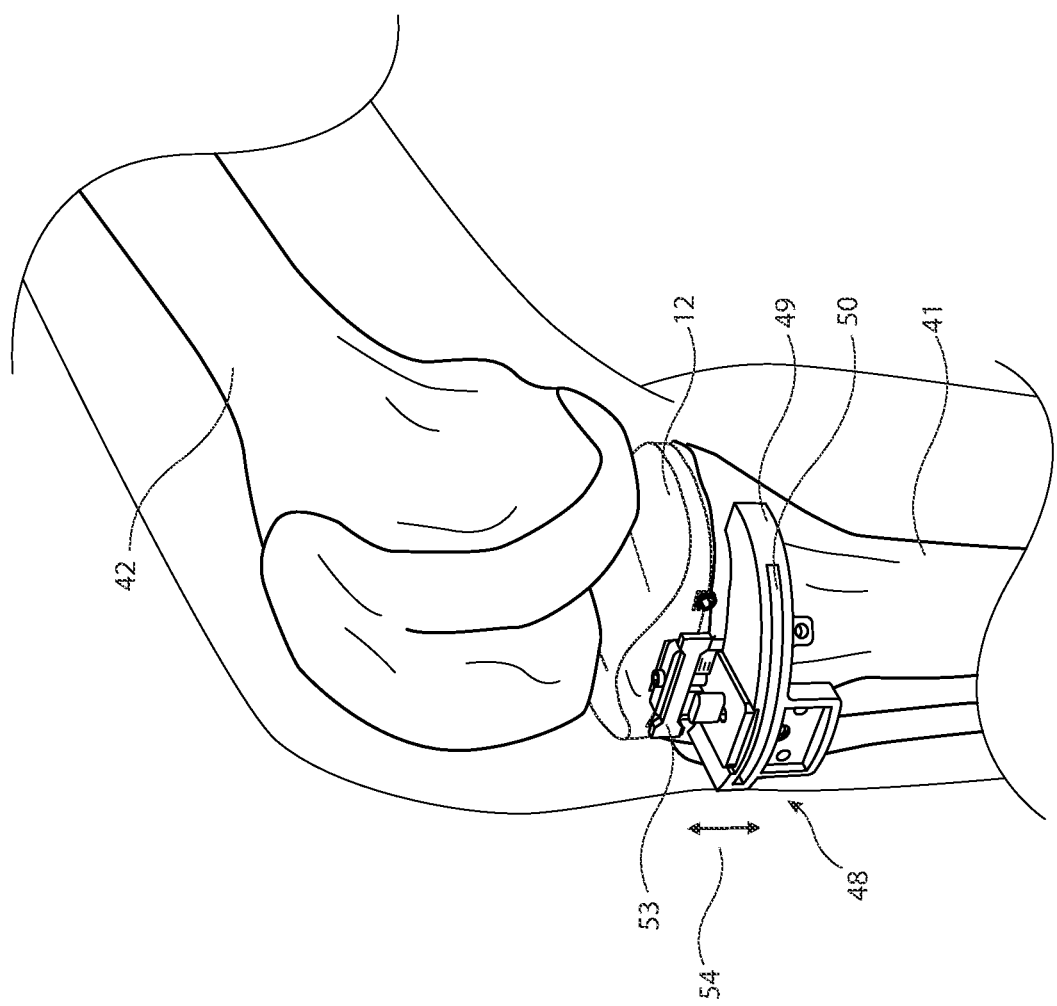

FIG. 7 shows the final bone resection of the proximal surface of the tibia cutting guide arrangement 48 mounted to the joint liner 12 wherein the engagement between the lug extensions 51 of the final bone resection of the proximal surface of the tibia cutting guide arrangement 48 and that pair of slots 47 on the front side 46 on the joint liner 12 means that the indicator slot 50 of the cutting guide 49 aligns in the same orientation as the referenced plane of the bottom surface 16 on the underside 14 of the joint liner 12.

As it is to be envisaged the pair of slots 47 of the joint liner 12, before any height adjustments of the user operable height adjustable extension tabs 24, 26 and 28 would be generally on the horizontal plane consistent with the initial resected surface 40 of the tibia 41 shown in FIG. 3.

None the less, as the user operable height adjustment extension tabs 24, 26 and 28 are adjusted to provide the stability gap this then alters the orientation of the bottom surface 16 on the underside 14 of the joint liner 12 and so to corresponding orientation of the slots 47 on the front side 46 of the joint liner 12.

Accordingly, as the pair of slots 47 of the joint liner 12 have now been offset through height adjustment the corresponding lug extensions 51 of the final bone resection of the proximal surface of the tibia cutting guide arrangement 48 will also be offset so that the indicator slot 50 of the cutting guide 49 will represent the same reference plane that exists on the bottom surface 16 on the underside 14 of the joint liner 12.

This mounted engagement between the joint liner 12 and the final bone resection of the proximal surface of the tibia cutting guide arrangement 48 shown in FIG. 7 provides for the first mounted position.

There is then the requirement to establish a second mounted position so that the cutting guide 49 and notably the correctly aligned indicator slot 50 now orientated the same as the reference plane on the bottom surface 16 on the underside 14 of the joint liner 12 can cut into a new layer of bone below the initial resected surface 40 of the tibia 41.

Through the use of the vertical support mount 53 included a part of the final bone resection of the proximal surface of the tibia cutting guide arrangement 48, the cutting guide 49 can be incrementally adjusted vertically there along the vertical support 53 shown by way of the arrow 54 in FIG. 7.

The vertical adjustment of the cutting guide 49 as part of the final bone resection of the proximal surface of the cutting guide arrangement 48 can be achieved through conventional incremental adjustments, such as through a ratchet, gearing, use of cams and so forth.

Figure 8:
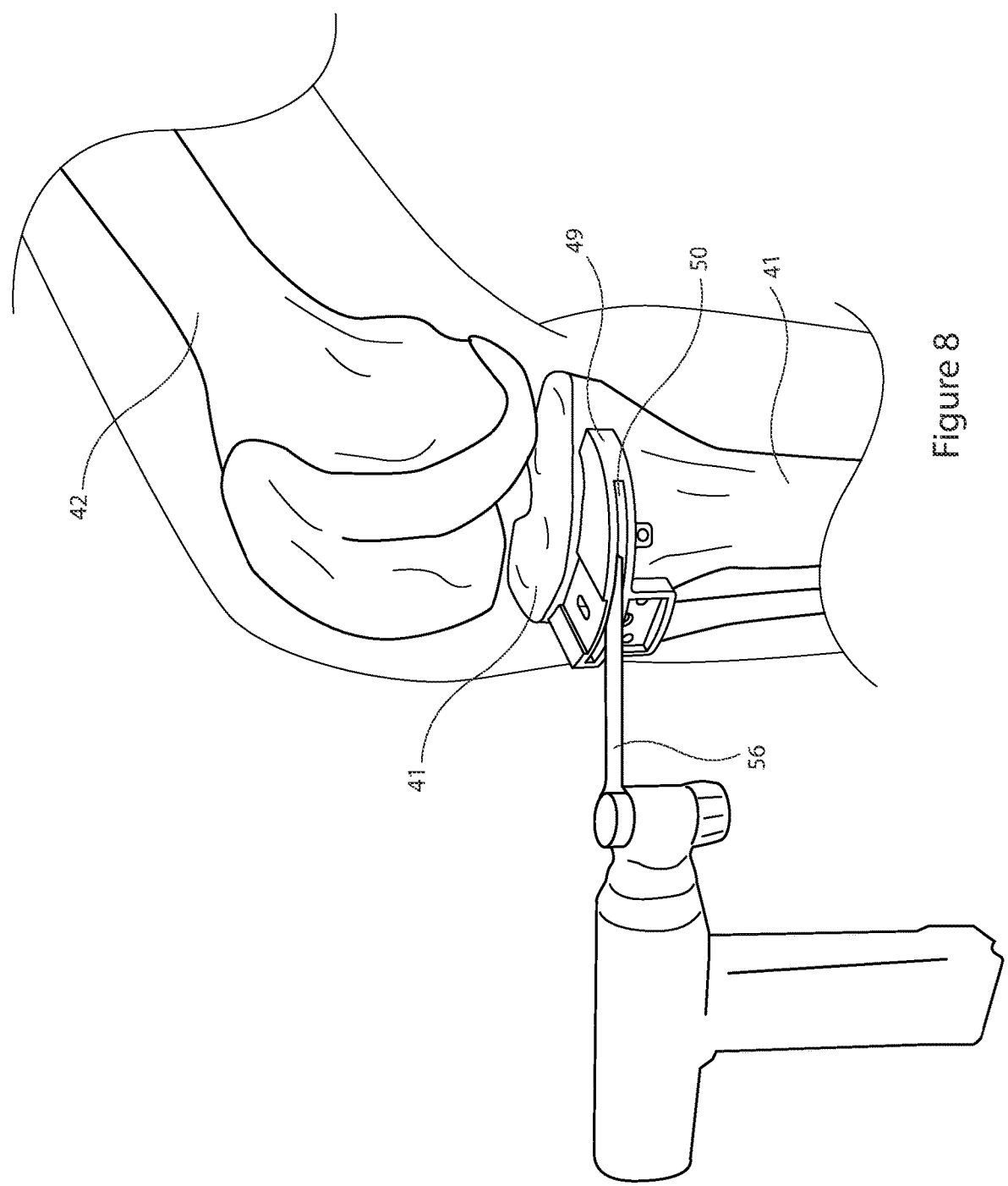

As seen in FIG. 8 once the cutting guide 49 has been lowered, the cutting guide 49 can then be separated from the final bone resection of the proximal surface of the tibia cutting guide arrangement 48. Wherein the vertical support 53 is also withdrawn.

Although the mounted means are not shown, the cutting guide 49 is mounted to the tibia 41 in the second mounted position which was provided for by the vertical mount 53 included as part of the final bone resection of the proximal surface of the tibia cutting guide arrangement 48.

Hence, the second mounted position has the cutting guide 49 fastenable in the correct vertical position for cutting into new bone below the initial resected proximal surface 40 of the tibia 41 as shown in FIG. 8.

Also the indicator slot 50 for the correct orientation is aligned as the same reference plane established on bottom surface 16 on the underside 14 of the joint liner 12.

However, the practicalities of the final resection requires the main infrastructure of the final bone resection of the tibia cutting guide arrangement 48 to be withdrawn. So once the second mounted position has been established the cutting guide 49 as shown in FIG. 8 would be then mounted though various pins and or bolts (not shown) to the tibia 41.

The cutting guide 49 is mounted with the indicator slot 50 correctly aligned and at the appropriate depth below the initially resected proximal surface 40 of the tibia 41, as seen in FIG. 8, wherein the blade or saw 56 is guidable and orientated through the slot 50 to enable for a final bone resection providing a profile of the proximal surface of the tibia, shown as 57 in FIG. 9 the same as the reference plane, ensuring a stability gap so that the tibia component insert of the prosthetic knee (not shown) is stable and balanced throughout the arc of motion in the artificial knee joint (not shown) that one would expect from an ideally balanced knee replacement.

FIGS. 10a and 10b show a further preferred embodiment of the invention focusing on the type of user-operable height adjustable extension tabs.

In the alternative preferred embodiment shown in FIGS. 10a and 10b, the user-operable height adjustable extension tabs (86, 88 and 90) are inflatable type bladders or balloons which as shown in FIG. 10a not being aerated and therefore are in a retracted configuration housed up into the underside (84) of the joint liner (80).

As shown by way of arrows (92) in FIG. 10b, the user-operable height adjustable extension tabs (86, 88 and 90) are ballooned out into the extended height adjusted positions.

Figures 11A, 11B:
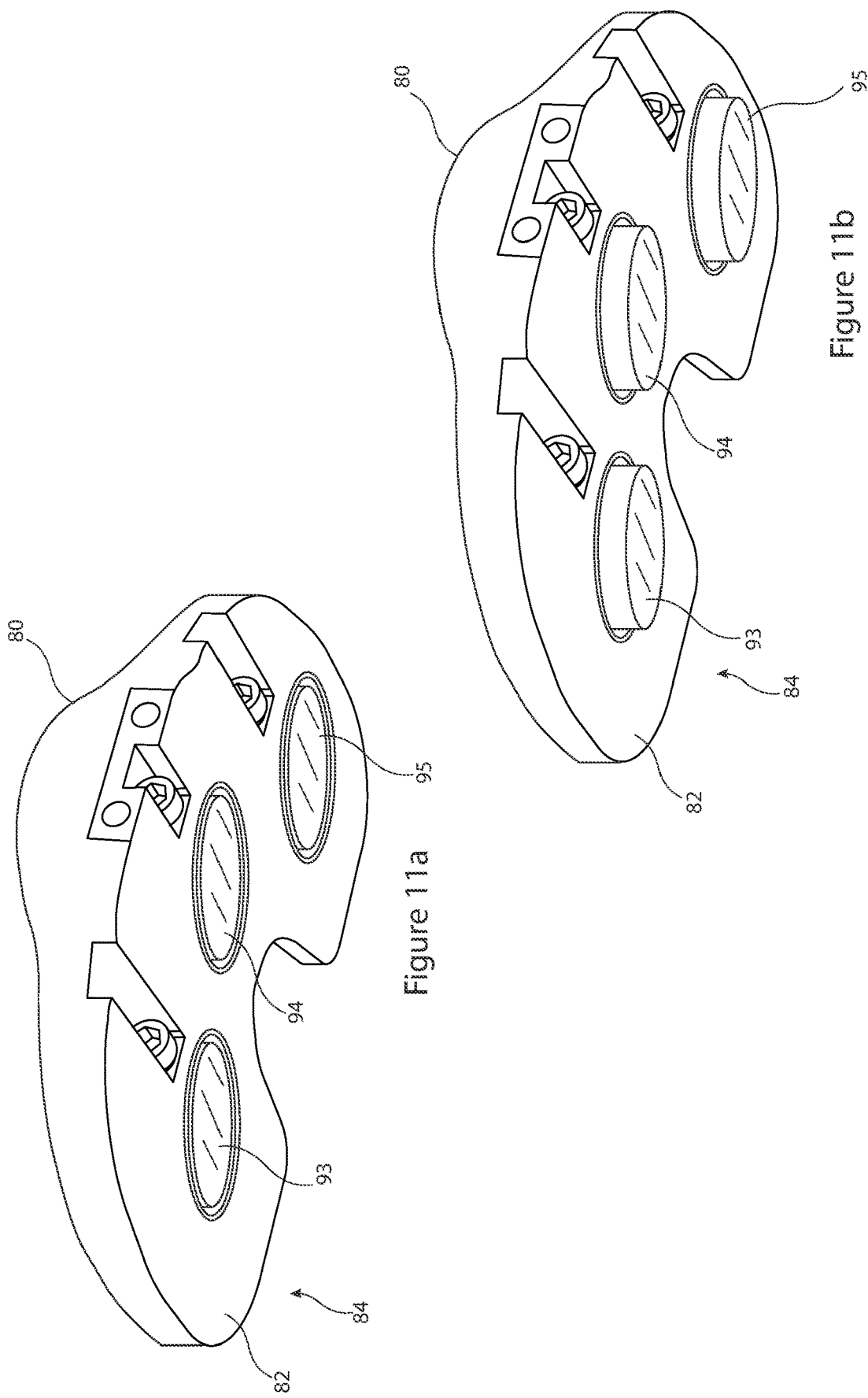

FIGS. 11a and 11b shown still further preferred embodiments of the user-operable height adjustable extension tabs (93, 94 and 95) which in this preferred embodiment shown for FIGS. 11a and 11b have the user-operable height adjustable extension tabs (93, 94 and 95) telescopically receivable into the underside (84) of the joint liner (80) and extendable out into their height adjustable required extended position as shown in FIG. 11b.

FIGS. 10a and 10b show a further preferred embodiment of the invention wherein the user-operable height adjustable extension tabs (110, 112 and 114), rather than being incorporated into a joint liner, are enclosed within slots (104, 106 and 108) internally defined into the underside (102) of the preparation plate (100) shown in FIGS. 12a and 12b. Arrows (121) in FIG. 12b represent vertical movement of the height adjustable extension tabs (110, 112 and 114).

There is still a degree of space savings by introducing these slots (104, 106 and 108) into the preparation plate (102) so that the starting point for the user-operable height adjustable extension tabs (110, 112 and 114) allows for the bottom surface (102) of the preparation plate (100) to remain flush with the surface of the initially resected proximal surface of the tibia.

Figure 13A:
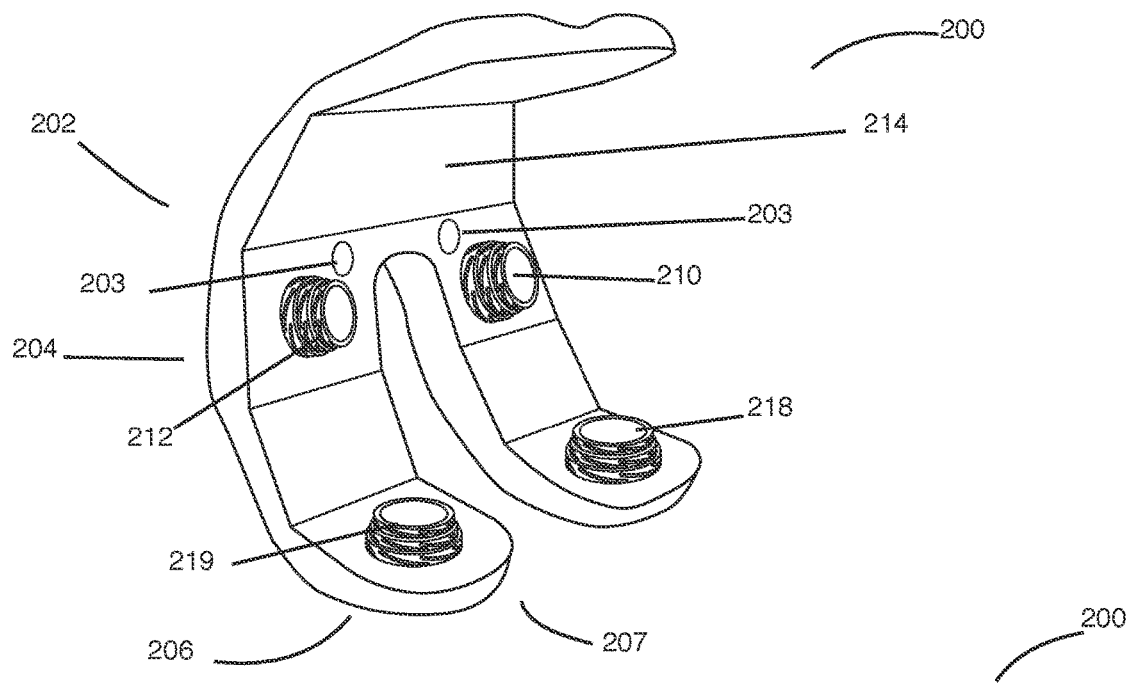
FIG. 13a is a rear perspective view of the arrangement for providing the proximal surface profile of the distal end of the femur and the posterior femoral condyle of the femur surfaces in a preferred embodiment of the invention.
Figure 13B:
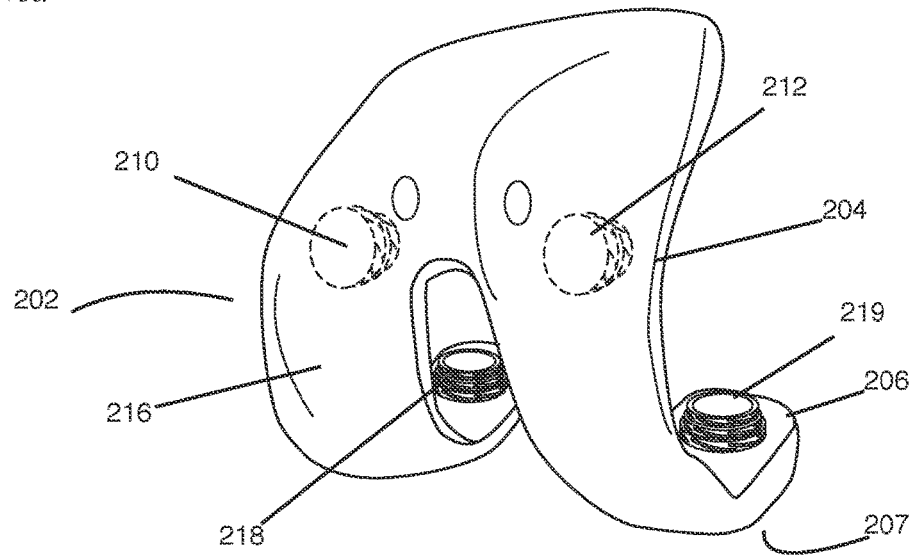

Referring to FIGS. 13a and 13b wherein the arrangement for providing the profiled proximal surface of the distal end of the femur and the posterior femoral condyle of the femur profiled surface for a femoral component of a prosthetic knee joint is shown generally as (200).

The arrangement (200) includes a femoral component (202) which has a generally C shaped configuration which is mountable to the femur which in the preferred embodiment shown in FIGS. 13a and 13b could be assisted by way of the mounting holes (203) such that this initial mounting of the femoral component (202) to the femur is such that vertical sections shown generally as (204) would be aligned with the distal end of the femur and the horizontal section (206) generally at the base (207) of the C configuration being generally aligning with the posterior femoral condyle of the femur.

The general C shape of the femoral component (202) has a generally flat top section (208).

Importantly for this invention the vertical section (204) of the femoral component (202) includes user-operable lateral adjustable extension tabs (210) and (212) on the inside or rear side (214) of the femoral component (202) as opposed to front side (216) of the femoral component shown in FIG. 13b.

These user-operable lateral adjustable extension tabs (210) (212) are adapted to engage an initially resected distal end of the femur so that when there is lateral adjustment of the femoral component (202) through the user-operable lateral adjustable extension tabs (210) (212) during gap measurements taken at extension, mid-flexion and flexion this provides for a final stability gap at the completion of these measurements where a distal end of the femur reference plane is defined upon or the orientation of the vertical section (204) of the femoral component (202).

The establishment of this femur reference plane defined on or by way of the orientation of the vertical section (204) of the femoral component (202) if then replicated as the final bone resection on the distal end of the femur as the same profile this will allow for the optimum balanced angular movement between the tibia component and the actual femoral component that will form part of the prosthetic knee joint throughout the arc of motion from extension, mid-flexion and flexion post surgery.

Importantly also for this invention, the femoral component (202) on the horizontal section (206) at the base (207) of the femoral component (202) includes user-operable height adjustable extension tabs (218) and (219) wherein these user-operable height adjustable extension tables (218) and (219) are adapted to engage the initially resected surface of the posterior femoral condyle of the femur so that when there is adjustment of the vertical height of the horizontal section of the femoral component (202) when measurements are taken at extension, mid-flexion and flexion, this defines the posterior femoral condyle reference plane upon that horizontal section (206) of the femoral component (202) and then if replicated as the final bone resection of the posterior femoral condyle, this will then provide for the optimum balanced angular movement between the femoral component and the tibia component that will form part of the prosthetic knee joint throughout an arc of motion from extension, mid-flexion and flexion.

Advantageously for this invention, rather than having an additional component to which the adjustable tabs are connected, as was the case in the applicant's earlier invention WO2017197462, in this instance those tabs are incorporated into a conventional femoral component which has now been modified.

With the elimination of the additional componentry required in the establishment of the relevant femur reference planes means there is a space saving required for the components to prepare the appropriate preparation of the proximal surfaces for the femur thereby minimizing the depth or amount of bone that needs to be initially cut at those end surfaces of the femur.

Figure 14A:
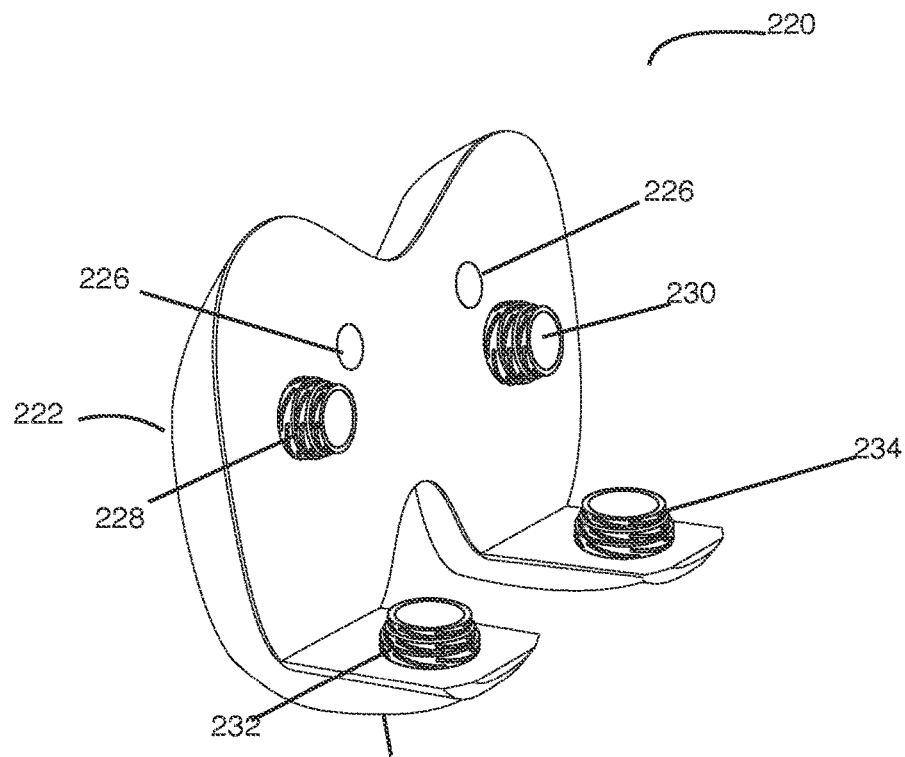
FIG. 14a is a further preferred embodiment of the invention illustrating an alternative shaped femoral component.
Figure 14B:
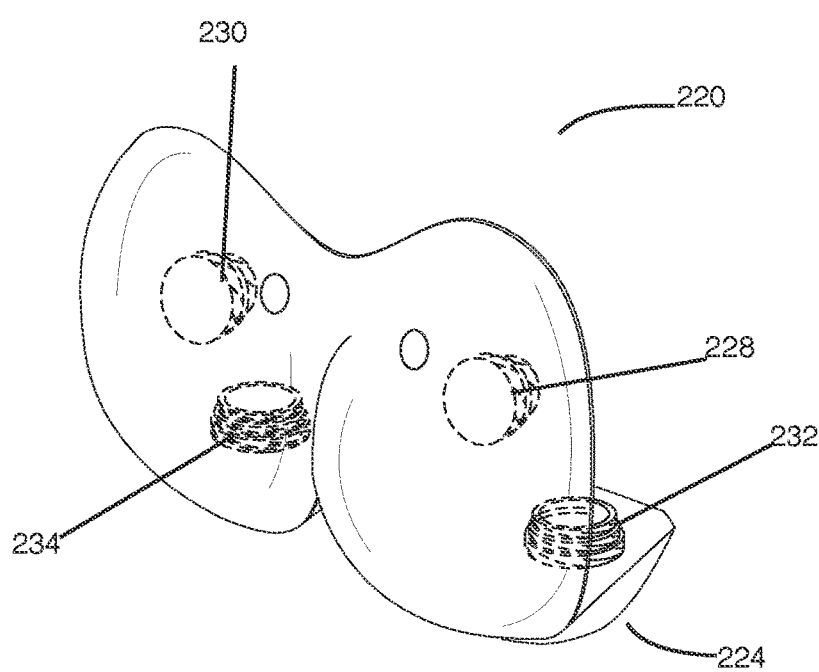

FIGS. 14a and 14b provide an alternative shape to the femoral component this time shown as (220) presenting a more L shaped appearance, including a vertical arm (222) and a horizontal arm (224).

The functioning and operation again of the femoral component (220) shown in FIGS. 14a and 14b remains the same as that discussed for FIGS. 13a and 13b with respect to the mountability of the femoral component (222) in a preferred embodiment can be through mounting holes (226) and then the adjustability to create the relevant reference planes by way of the user-operable lateral adjustable extension tabs (228) and (230) on the vertical arm (222) of the femoral component (220) and then the user-operable height adjustable extension tabs (232) and (234) of the vertical section (224) of the femoral component (220).

Figure 15A:
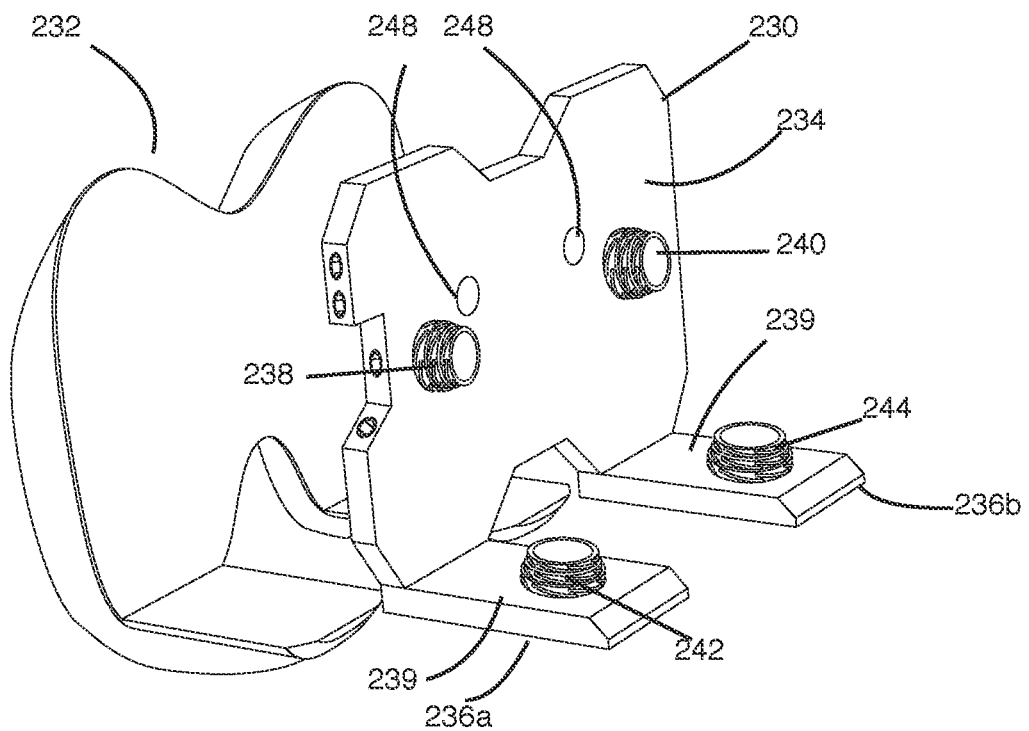
FIGS. 15a and 15b show rear and front perspective views of a further embodiment of the invention wherein the arrangement includes the use of an L shaped femoral clamp.
Figure 15B:
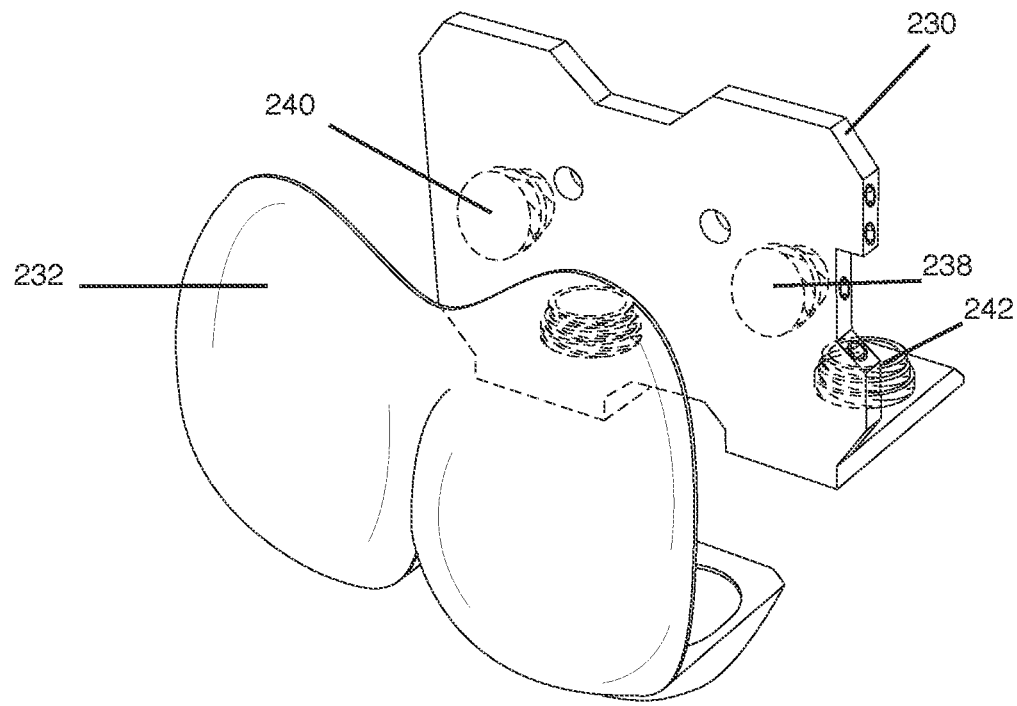

FIGS. 15a and 15b show still a further preferred embodiment of the invention where there is minimizing of the depth that is required to be cut off the proximal surface of the femur in the initial resection part of the surgery by incorporating the user-operable lateral adjustable extension tabs (238) and (240) at least partially within the rear side (234) of the generally L shaped femoral clamp (230).

The rear surface (234) of the vertical arm (235) of the generally L shaped femoral clamp (230) is orientated so that the user-operable lateral adjustable extension tabs (238) and (240) are able engage with the initially resect a distal end of the femur and wherein the user-operable height adjustable extension tabs (242) and (244) as part of the respective horizontal arm sections (236a) and (236b) are then adapted to engage with the initial resected surface of the posterior femoral condyle of the femur.

Once again this embodiment shown in FIGS. 15a and 15b can be distinguished from the applicant's earlier arrangement shown in WO2017197462 in that the relevant user-operable extension tabs positioned on both the vertical and horizontal arms, instead of engaging with the front plate (232) are placed on the inside surface of the vertical arm and the top surface (239) of the horizontal section (236a) and (236b) and importantly at least partially enclosed within this rear surface (234) and the top surface (239) when the extension tabs (238), (240), (242) and (244) are in a generally retracted position.

The invention claimed is:

1. An arrangement for the preparation of the proximal surface of the tibia of a patient for a tibia component of a prosthetic knee joint, said arrangement including:
   a joint liner including:
      a body having an underside surface to face an initial resected tibia bone top surface, and an upper articulated surface to engage a femoral component of the prosthetic knee joint, and a plurality of user-operable height adjustable extension tabs each height adjustable relative to the underside surface of said joint liner to directly contact the initial resected tibia bone top surface, such that a height adjustment of said plurality of user-operable height adjustable extension tabs in each of extension, mid-flexion and flexion positions of the prosthetic knee joint orients the underside surface of the joint liner to define a tibia reference plane, wherein a final bone resection of the proximal surface of the tibia consistent with the orientation of said tibia reference plane provides for balanced angular movement between the tibia component and the femoral component of the prosthetic knee joint throughout an arc motion from the extension position, through mid-flexion position, to the flexion position of the prosthetic knee joint.

2. The arrangement of claim 1 wherein the joint liner includes a plurality of slots on the underside surface of the joint liner in which corresponding ones of the plurality of user-operable height adjustable extension tabs can be enclosed or at least substantially enclosed therein.

3. The arrangement of claim 1 wherein the plurality of user-operable height adjustable extension tabs includes three operable height adjustable extension tabs and wherein the joint liner includes three corresponding slots wherein each respective slot of the joint liner encloses a corresponding user-operable height adjustable extension tab.

4. The arrangement claim 1 wherein each user-operable height adjustable extension tab is height adjustable utilising mechanical, hydraulic, electrical, electronic and/or a pneumatic drive action.

5. The arrangement of claim 1 wherein each user-operable height adjustable extension tab is in communication with a corresponding user-engageable knob-so as to be height adjustable through manipulation of said knob.

6. The arrangement of claim 1 wherein each user-operable height adjustable extension tab is remotely height adjustable by way of radio signals.

7. The arrangement of claim 1 wherein each user-operable height adjustable extension tab is height adjustable by expanding and deflating a bladder.

8. The arrangement of claim 7 wherein the expanding and deflating of the bladder is by aeration and/or fluid control, and wherein aeration is provided by pneumatics.

9. The arrangement of claim 1 wherein the final bone resection of the proximal surface of the tibia includes an electronic system arrangement including an input signal, wherein the input signal into the electronic system arrangement provides tibia reference plane measured data information, wherein the tibia reference plane measured data information includes the orientation in space, angle and/or positioning of the tibia reference plane defined by the underside surface of the joint liner;

said electronic system arrangement configured to respond to the inputted signal of the tibia reference plane measured data information to communicate electrical energy in the form of an output action to align a blade and/or cutting implement at an angle such that resecting of the bone across at or below the proximal surface of the tibia at the alignment of the blade and/or cutting implement provided by the tibia reference plane measured data information replicates the tibia reference plane on the proximal surface of the final resected tibia.

10. The arrangement of claim 1 further comprising:
a tibia cutting guide arrangement for making the final bone resection of the proximal surface of the tibia, the tibia cutting guide arrangement including a cutting guide having an indicator, wherein the indicator provides a reference guide for a cutting blade or saw to cut the final bone resection of the proximal surface of the tibia; and a mounting arrangement-configured to provide a first mounted position between said joint liner and said tibia cutting guide arrangement, wherein the indicator of the cutting guide is aligned with the tibia reference plane defined by the underside surface of the joint liner, and a second mounted position wherein the indicator of the cutting guide is adjustable below the initial resected proximal surface of the tibia.

11. The arrangement of claim 10 wherein the mounting arrangement includes at least one slot and at least a corresponding lug.

12. The arrangement of claim 11 wherein the joint liner includes at least one slot and the tibia cutting guide arrangement includes a or corresponding lug for the or each slot or wherein the joint liner includes at least one lug and the tibia cutting guide arrangement includes a or corresponding slot for the or each lug.

13. The arrangement of claim 12 wherein there are at least a pair of slots on the front side of the joint liner and a pair of corresponding lugs protruding out from the front of the tibia cutting guide arrangement or wherein there are at least a pair of lugs protruding out a front side of the joint liner and a pair of corresponding slots in the tibia cutting guide arrangement.

14. The arrangement of claim 13 further comprising a vertical support s along which the cutting guide is vertically.

15. The arrangement of claim 14 wherein the vertical support is adapted to incrementally adjust and position the cutting guide vertically adjustable.

16. The arrangement of claim 15 wherein the vertical incremental adjustment of the cutting guide along the vertical support includes a ratchet arrangement.

17. The arrangement of claim 15 wherein the vertical incremental adjustability of the cutting guide along the vertical support can include a clutch, intermediate gearing and cams.

18. The arrangement of claim 16 wherein the indicator includes a slot to guide a saw or blade to complete the final bone resection of the proximal surface of the tibia, the slot orienting the saw or blade.

19. An arrangement the preparation of the proximal surface of the tibia of a patient for a tibia component of a prosthetic knee joint, said arrangement including:
a joint liner including:
a body having an underside surface, and an upper articulated surface to engage a femoral component of the prosthetic knee joint, and
a plurality of user-operable height adjustable extension tabs each height adjustable relative to the underside surface of said joint liner to engage an initial resection surface of the prosthetic knee joint, such that a height adjustment of said plurality of user-operable height adjustable extension tabs in each of extension, mid-flexion and flexion positions of the prosthetic knee joint orients the underside surface of the joint liner to define a tibia reference plane, wherein a final bone resection of the proximal surface of the tibia consistent with the orientation of said tibia reference plane provides for balanced angular movement between the tibia component and the femoral component of the prosthetic knee joint throughout an arc motion from the extension position, through mid-flexion position, to the flexion position of the prosthetic knee joint, wherein each user-operable height adjustable extension tab is telescopically extendable and retractable to and from the underside surface of the joint liner or from within corresponding slots located on the bottom side of the underside surface of the joint liner.

\* \* \* \* \*